(12) United States Patent
Hickok

(10) Patent No.: US 6,910,889 B1
(45) Date of Patent: Jun. 28, 2005

(54) ULTRASONIC SURGICAL DENTAL TOOL HAVING A RASP TIP

(75) Inventor: Teresa R. Hickok, Bonita, CA (US)

(73) Assignee: San Diego Swiss Machining, Inc., San Diego, CA (US)

( * ) Notice: Subject to any disclaimer, the term of this patent is extended or adjusted under 35 U.S.C. 154(b) by 417 days.

(21) Appl. No.: 09/704,855

(22) Filed: Nov. 2, 2000

(51) Int. Cl.⁷ .................................................. A61C 3/03
(52) U.S. Cl. ........................ 433/119; 433/102; 433/166
(58) Field of Search ................................ 433/118, 119, 433/141, 142, 143, 144

(56) References Cited

U.S. PATENT DOCUMENTS

| | | | |
|---|---|---|---|
| 3,563,233 A | | 2/1971 | Bodine |
| 4,019,254 A | | 4/1977 | Malmin |
| 4,283,174 A | * | 8/1981 | Sertich ........................ 433/119 |
| 4,283,175 A | * | 8/1981 | Nash ........................... 433/119 |
| 4,608,019 A | * | 8/1986 | Kumabe et al. ......... 433/119 X |
| 4,731,019 A | | 3/1988 | Martin |
| 5,704,787 A | | 1/1998 | Hickok et al. |
| 5,725,370 A | * | 3/1998 | Himeno et al. ......... 433/119 X |
| 5,816,808 A | | 10/1998 | Gambarini et al. |
| 6,273,717 B1 | | 8/2001 | Hahn et al. |
| 6,514,076 B1 | | 2/2003 | Bleiweiss et al. |

FOREIGN PATENT DOCUMENTS

| | | |
|---|---|---|
| DE | 296 03 974 U1 | 6/1996 |
| DE | 197 54 879 A1 | 6/1999 |
| FR | 2806292 A1 | 3/2000 |
| WO | PCT/EP98/04272 | 7/1998 |
| WO | PCT/US00/07858 | 3/2000 |

* cited by examiner

Primary Examiner—Nicholas D. Lucchesi
(74) Attorney, Agent, or Firm—Lewis Rice & Fingersh LC

(57) ABSTRACT

A dental tool for use with an ultrasonic transducer, includes an elongated unitary shaft member having a longitudinal axis, a proximal end and a distal end having an outer surface, an attachment member at the proximal end to enable detachable attachment to an ultrasonic transducer; and a cutting surface defined by a plurality of grooves on the outer surface forming sharp edges.

12 Claims, 2 Drawing Sheets

ULTRASONIC SURGICAL DENTAL TOOL HAVING A RASP TIP

FIELD OF THE INVENTION

This invention relates generally to ultrasonic dental tools and pertains more particularly to special ultrasonic dental tools for periodontal disease.

BACKGROUND

In the past decade, ultrasonic dental tools have come into greater use and have begun to replace most rotary power and hand dental tools for drilling, cutting, shaping, cleaning and polishing teeth. Most of the powered prior art dental tools were powered by rotating electric or air motors. The tools useable with these power units were limited to rotating drills, cutters and grinders. The ultrasonic powered dental tools of recent years have several advantages over the prior art devices for most applications. Among the advantages are that they are smaller and lighter in weight and can be more easily manipulated in and around dental structures in the oral cavity.

The ultrasonic power units have an entirely different type of motion than the rotary motion of air and electric motor powered units of the past. The motion imparted to the tool by an ultrasonic power unit is usually a small amplitude very high frequency or velocity oscillation or reciprocation. This motion is imparted to the working tip of the tool. The use of ultrasonic powered tools has resulted in the need for the development of entirely different types and sizes of tools. While many tools have been developed and are available for use with ultrasonic power units, there is a need for additional tools designed and configured to perform periodontal procedures.

Periodontal disease affects several areas in the oral cavity. These areas include the root area of the tooth, the bone and the gums. Typical treatment involves removal of the diseased portion of the structure of these areas. This includes planing and smoothing of the root surfaces and the bone. It also involves curettage of the affected tissue.

This treatment requires special tools designed to effectively carry out these procedures. The prior art tools, while helpful are not entirely satisfactory. Among the prior art patents disclosing tools designed for this purpose are U.S. Pat. No. 4,283,175 to Nash, U.S. Pat. No. 4,353,696 to Martin, U.S. Pat. No. 4,731,019 to Martin and U.S. Pat. No. 5,704,787 granted to applicant.

Therefore, there is a need for improved ultrasonic dental tools formed of a suitable strong and durable heat resistant material with suitable structure and configurations for effectively performing periodontal procedures.

SUMMARY OF THE INVENTION

A primary objective of this invention is to provide an improved ultrasonic dental tool having a tip that is formed of durable high strength heat resistant material having a configuration for performing periodontal procedures.

In accordance with a primary aspect of the present invention a dental tool for use with an ultrasonic transducer comprises an elongated unitary shaft member having a proximal end and a distal end, attachment means at said proximal end to enable detachable attachment to an ultrasonic transducer; and a cutting surface at said distal end defined by a plurality of grooves forming sharp edges on said surface.

BRIEF DESCRIPTION OF DRAWINGS

The objects, advantages and features of this invention will be more readily appreciated from the following detailed description, when read in conjunction with the accompanying drawing, in which.

DETAILED DESCRIPTION OF PREFERRED EMBODIMENTS

Figure 1:
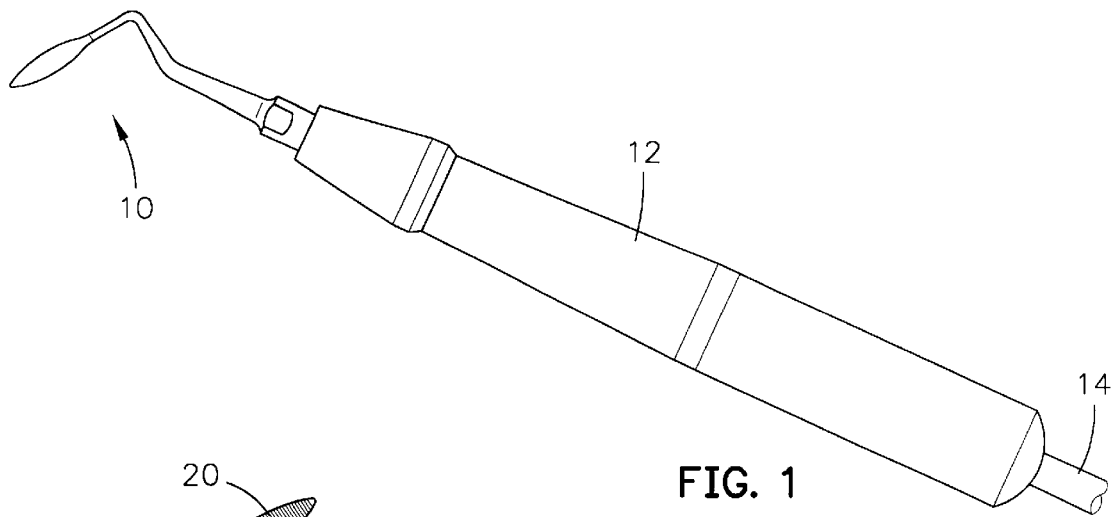
FIG. 1 is a side elevation view of an ultrasonic hand piece equipped with dental tool constructed in accordance with a preferred embodiment of the invention.

The present invention is described with reference to preferred embodiments of the invention as illustrated in the drawings. While this invention is described in terms of the best mode for achieving this invention's objectives, it will be appreciated by those skilled in the art that variations may be made in view of these teachings without deviating from the spirit or scope of the invention.

Figure 2:
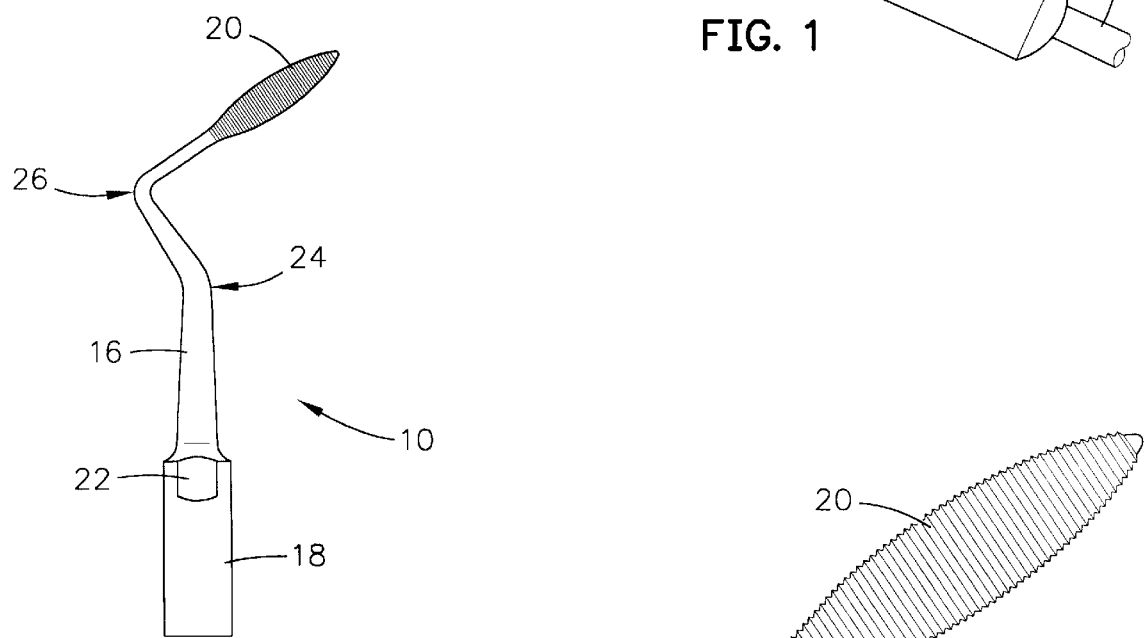
FIG. 2 is a side elevation view of the dental tool of FIG. 1.
Figure 3:
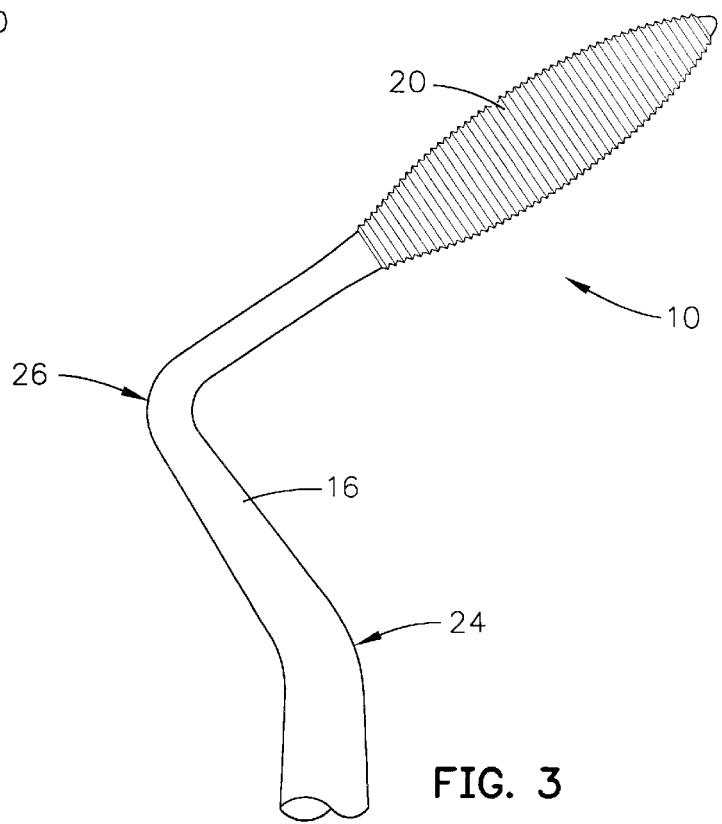
FIG. 3 is an enlarged a side elevation view of a portion of the dental tool of FIG. 1.

Referring to FIGS. 1 and 2 of the drawings there is illustrated an exemplary embodiment of a tool for dental surgical operations, in accordance with the present invention, designated generally by the numeral 10. The tool 10 is shown mounted in an end of an ultrasonic hand piece 12 in which is mounted an ultrasonic transducer which generates ultrasonic vibrations transmitted to the tool. The ultrasonic transducer or motor mounted in the hand piece is connected by a conductor within a line 14 to a converter box (not shown). The line 14 may also contain a water line or tube for conveying water or other fluids to the working tip. The tool 10 may also be formed with means to get water or fluid to the working surface of the surgical tip of the tool. The ultrasonic transducer (not shown) within the hand piece is connected to a shaft (not shown) that extends from the front of the hand piece to which the tool is attached by a suitable detachable connection.

The tool, as illustrated, comprises an elongated shaft 16 having connecting means 18 at a first or proximal end and a rasp like cutting surface 20 at a second or distal end. The connecting means is preferably in the form of a threaded socket (not shown) for detachably mounting on the end of a shaft. However, it may take any other suitable form. A flat 22 is provided on each side for engagement by a wrench or the like for rotating the tool and tightening and loosening the tool. The connecting means may also be a quick connect type connector such as that disclosed in my copending application Ser. No. 09/326,046 filed Jun. 4, 1999, and incorporated herein by reference.

The tool is formed with an elongated tapered shank or shaft 16 that is bent or shaped and configured to position the working tip at a desirable position relative to the hand piece.

The shaft has a first bend 24 about half way between the proximal or attachment end and the distal or working end. A second bend 26 is positioned between the first bend and the distal end so that the distal end portion is curved away from the primary axis of the shaft to form what is commonly called a working tip. The tip as used herein means that portion of the tool at the outer or distal end configured to have a working surface or edge. 'The first bend 24 in the shaft of the tool is shown to be approximately ½ of the length along the tapered shaft from the connecting member to the tip. It may be anywhere between about ⅓ and ⅔ along the length of the shaft and together with the second bend is devised to position the working tip at a convenient position and angle for ease of holding and use by the user. The shaft is configured to positions the working tip at a convenient angle with respect to the hand piece being held to enable it to be positioned and manipulated in the oral cavity by the user.

The shaft of the tool may have a uniform taper along its length or it may have a compound taper such that it tapers a slight degree along a first portion and tapers at a slightly higher angle along the remainder of the shaft. The overall tool is constructed and configured to be tuned to and be matched to the impedance of the ultrasonic generator.

The working tip 20 of the tool shaped and configured to position in a necessary work area. The tool as shown has a somewhat bulbular or football form, and is positioned or formed at the very outer end or tip of the shaft. The working tip begins to increase in diameter at the inner end from that of the shaft and increases to a maximum diameter at the center and decreases again down to minimum diameter or substantially a point at the very outer tip. The working tip is formed with a generally file or rasp cutting surface which is formed with or by a plurality closely parallel grooves in the surface forming sharp cutting edges at the surface of the tool between the grooves. In the illustrated embodiment, the grooves extend in a parallel array around the circumference of the tool tip. The grooves are of a generally V-shape and form a sharp edge at the surface between the adjacent grooves.

Figure 4:
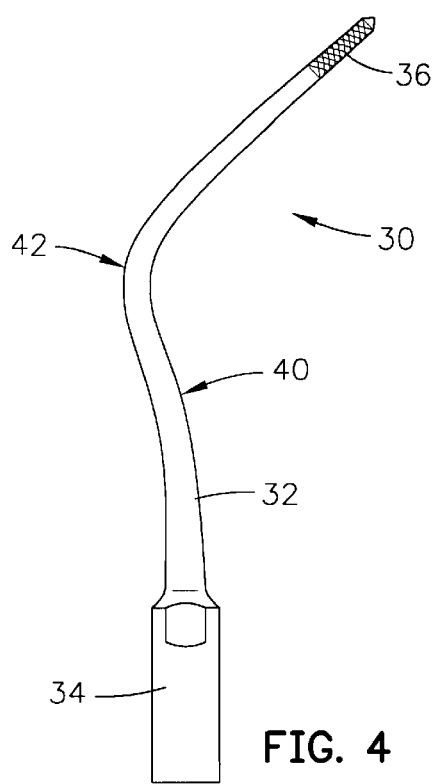
FIG. 4 is a side elevation view of an alternate embodiment of an ultrasonic dental tool of the invention.
Figure 5:
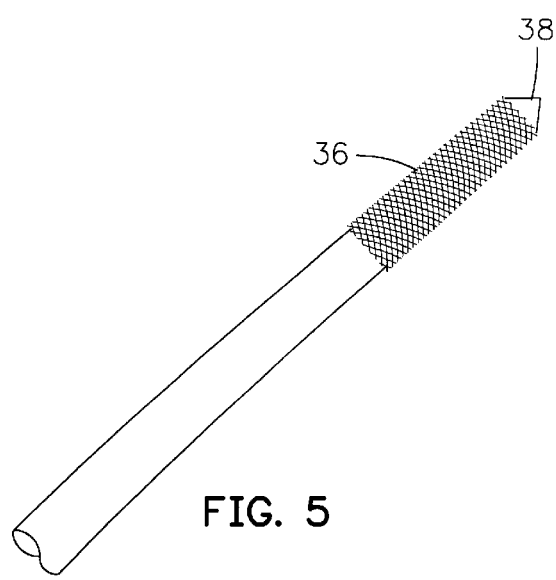
FIG. 5 is an enlarged a side elevation view of a cutting tip portion of the dental tool of FIG. 4.

Referring now to FIGS. 4 and 5, an alternate embodiment of the cutting tool is illustrated and designated generally by the numeral 30. In this embodiment, the shaft or shaft 32 is tapered down from a connecting means or member 34 substantially identical to that of the previous embodiment. The tool has a working tip 36 formed or configured to have a generally cylindrical configuration with a surface area and length that is about three times the diameter of the shaft at the outer tip. The working surface is shown to be about the same diameter of the shaft at the end thereof. However, it may be larger or smaller as desired to perform a particular operation. The very outer end 38 of the shaft has a generally conical shape tapering down to a point.

The working surface 36 is formed with a knurl-like surface by a series of helical extending parallel grooves formed in the surface of the tip. A first plurality of grooves extend in a clockwise direction about the shaft. A second set of groves extend in a counterclockwise direction about the shaft crossing the first set forming generally diamond shaped areas. The grooves form sharp cutting edges at the intersection of the groves with the surface of the shaft. When the grooves are sufficiently close, they form pyramid or diamond shaped projections with a sharp point.

The shaft 32 is formed with first and second bends 40 and 42 as in the previous embodiment to properly position and orient the a tip relative to the hand piece. However, the bends are more gentle with a larger radius of curvature than in the prior embodiment. The bends as in the prior embodiment positions and orients the blade relative to the shaft and the hand piece for ease of manipulation by the user of the tool. The cutting edge is angled to extend at a desirable angle relative to the hand piece such that the overall cutting surface or edge is at a comfortable working angle to the hand piece for the user.

Figure 6:
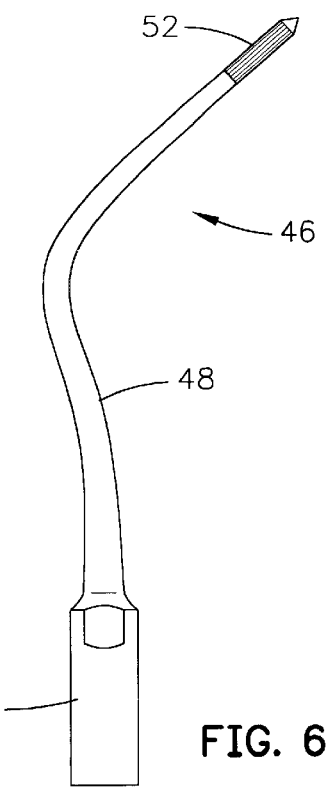
FIG. 6 is a side elevation view of another embodiment of an ultrasonic dental tool.
Figure 7:
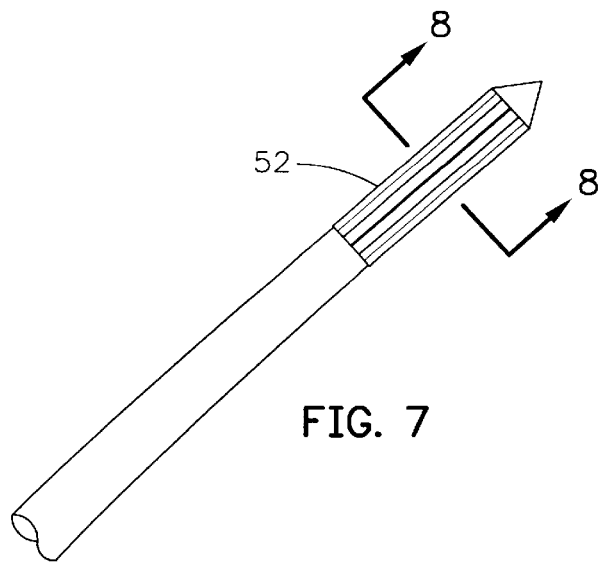
FIG. 7 is an enlarged a side elevation view of a cutting tip portion of the dental tool of FIG. 6.
Figure 8:
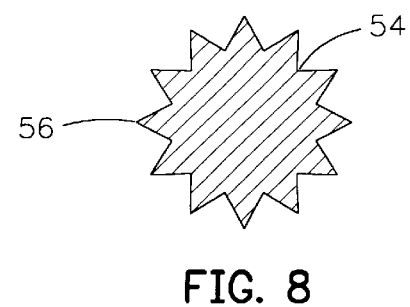
FIG. 8 is an enlarged a end view of a cutting tip portion of the dental tool of FIG. 6.

Referring to FIGS. 6–8, another embodiment of the tool is illustrated designated generally by the numeral 46 and having shaft 48 with a connector 50 and a working tip 52. In this embodiment the shaft is substantially the same in basic construction and configuration as in the previous embodiment with substantially the same curves and bends. The working or cutting tip has a generally cylindrical configuration with a diameter about the same as that of the shaft at the end thereof The cutting surface is formed by a plurality of axially extending parallel grooves 54 formed in the surface of the outer end of the shaft. The grooves as illustrated are spaced apart around the circumference of the end of the shaft forming lands 56 between the grooves. A cutting edge is formed at the intersection of the groove and the surface of the shaft. In an another embodiment, the grooves may be positioned closer together so that they substantially intersect at the surface of the shaft. This would present a greater number of cutting edges for a given diameter shaft. It would present cutting edges that could be made sharper than in the prior embodiment.

It is contemplated that a set of the tools will be provided having lengths, and angles that may vary with the lengths and shape of the cutting surface. The cutting surface will have a length may vary between about two and about four times the diameter of the shaft. Exemplary dimensions of a typical exemplary embodiment are with a total length of the tool of about 1.9 inches with the shaft and tip having a length of approximately 1.5 inches. In one embodiment, the shaft has a short cylindrical portion of approximately 0.30 inches from the connecting member and a taper from about 0.085 down to 0.40 proximate the center thereof and further tapering from that point to approximately the juncture of the working tip. An exemplary working tip of the FIG. 1 and 2 embodiment may have a cutting surface length along its axis of about 0.375 with a diameter of about 0.085. It will be appreciated that these may vary to meet the particular needs of the particular application.

The tools in accordance with this invention may be made of any number of suitable materials such as stainless steel and various alloys thereof. The tool is preferably constructed of a good medical grade of stainless steel, but may be constructed of a titanium alloy of a medical grade. Suitable stainless steels include, but are not limited to, 13-8MO, and 17-4PH. Medical grade alloy means a material that may be used in contact with food and with a patients body without undergoing a chemical reaction.

The tools may also be made of titanium and various alloys thereof as disclosed in my U.S. Pat. No. 5,836,765, incorporated herein by reference as though fully set forth. A titanium alloy that the inventor has found preferable in the present and similar applications is identified as 6AL/4V ELI & CP Grade 4 and is available from President Titanium of Hanson, Mass. The inventor has found this material to be sufficiently hard, durable and flexible to resist breakage under use. Likewise, various coatings may be applied to the tip to achieve its purpose.

The tools are formed by machining on a lathe or milling machine or combinations thereof. The tools, after formation, may go through various hardening and other treatment procedures before use such as disclosed in my U.S. Pat. No. 5,1704,787, incorporated herein by reference as though fully set forth. The abrasive or cutting surfaces of the tools may also be coated with a thin coating of a metal nitride such as disclosed in the aforementioned '787 patent.

In general, the preferred overall process for manufacturing the tips is as follows. A suitable stock is selected and an ultrasonic dental tool is manufactured typically by machining to form the shaft with connector and tip of the desired configuration. The abrasive or cutting surface is formed at the outer tip by a machining procedure to cut the grooves and form the cutting edges. The shaft is then bent into the proper shape or configuration to orient and position the tip as desired. The next step in the process is to heat treat the steel after the roughing step to achieve a Rockwell-C hardness rating preferably or the order of about 40–42. Heat treating is a well known process that involves heating and cooling of a metal in the solid state for the purpose of obtaining certain desirable properties including increased hardness.

A metal nitride coating may be applied to the roughened outer surface. Preferably, the metal element is selected from the group consisting of Zirconium (Zr) and Titanium (Ti). Between a Ti—N and Zr—N coating, the latter is the hardest at about 3000 Vickers while the former is about 2800 Vickers. Either metal nitride provides a very hard surface tip with far less cost than those using diamonds. Further, one can expect long wear from tips created by the process of this invention because Ti—N and Zr—N are both highly resistant to abrasion and corrosion.

When the heat treating is followed by the application of a metal nitride coating the result is an extremely hard tip having very desirable cutting abilities. The coating may be applied by any well-known technique in the art. While not desiring to be limited to any particular method of coating, the inventors have discovered that the well-known technique of using physical vapor deposition equipment employing cathodic arc techniques is a satisfactory way to deposit thin films of the metal nitrides on dental surgical tips. The coating is preferably applied very thinly so that its average thickness is about 0.0002 inches. An advantage of such a thin coating is that very small diameter tips can be created that are extremely hard and yet abrasive. Such small diameter tips are desirable for microsurgery.

In operation, the tools described herein were developed predominantly for the periodontal treatment in root surfaces, soft tissue, and bone. The fine sharp cutting surfaces of the present tools can plane and abrade cementum and curette and contour the gingival tissue and alveolar bone. These tools enable the creation of smoother contoured surfaces than the prior art. The configuration of the shaft of the tool with bends and curvatures enable them to be positioned and used in unusually close quarters in the oral cavity. In view of the above description, it is possible that numerous modifications and improvements will occur to those skilled in the art, which are within the scope of the appended claims. Therefore, this invention is not to be limited in any way except by the appended claims.

I claim:

1. A dental tool for use with an ultrasonic transducer, the tool comprising:
   an elongated unitary shaft member having a longitudinal axis, a proximal end and a distal end having an outer surface; and
   a connector at said proximal end to enable detachable attachment to an ultrasonic transducer;
   wherein said outer surface on said distal end includes a cutting surface defined by two pluralities of grooves in said cutting surface, said first plurality of grooves extending in a generally clockwise direction about said shaft member, said second plurality of grooves extending in a generally counterclockwise direction about said shaft member and crossing said first plurality; and
   wherein said first plurality of grooves and said second plurality of grooves are arranged sufficiently close to form pyramid shaped projections between said crossings.

2. The tool of claim 1, wherein said shaft has at least one bend intermediate said proximal end and said distal end so that said distal end extends at an angle to said axis.

3. The tool of claim 1, wherein said distal end extends at an angle of between about 30 and 60 degrees to said shaft.

4. The tool of claim 1, wherein said outer surface is formed with a knurl-like surface.

5. The tool of claim 1, wherein each of said pluralities comprise parallel grooves.

6. The tool of claim 1, wherein said pyramid shaped projections have sharp points.

7. A dental tool for use with an ultrasonic transducer, the tool comprising:
   an elongated unitary shaft member having a longitudinal axis, a proximal end and a distal end having an outer surface; and
   a connector at said proximal end to enable detachable attachment to an ultrasonic transducer;
   wherein said outer surface on said distal end includes a cutting surface defined by two pluralities of grooves in said cutting surface, said first plurality of grooves extending in a generally clockwise direction about said shaft member, said second plurality of grooves extending in a generally counterclockwise direction about said shaft member and crossing said first plurality; and
   wherein said first plurality of grooves and said second plurality of grooves are arranged sufficiently close to form diamond shaped projections between said crossings.

8. The tool of claim 1, wherein said shaft has at least one bend intermediate said proximal end and said distal end so that said distal end extends at an angle to said axis.

9. The tool of claim 1, wherein said distal end extends at an angle of between about 30 and 60 degrees to said shaft.

10. The tool of claim 1, wherein said outer surface is formed with a knurl-like surface.

11. The tool of claim 1 wherein each of said pluralities comprise parallel grooves.

12. The tool of claim 1 wherein said diamond shaped projections have sharp points.

* * * * *